(12) United States Patent
Gordziel

(10) Patent No.: US 6,586,469 B2
(45) Date of Patent: *Jul. 1, 2003

(54) ANTIHISTAMINIC/ANTITUSSIVE COMPOSITIONS

(75) Inventor: Steven A. Gordziel, BelleMead, NJ (US)

(73) Assignee: Medpointe Healthcare Inc., Somerset, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 10/035,976

(22) Filed: Oct. 26, 2001

(65) Prior Publication Data

US 2002/0156021 A1 Oct. 24, 2002

Related U.S. Application Data

(63) Continuation of application No. 09/625,422, filed on Jul. 25, 2000, now Pat. No. 6,306,904.

(51) Int. Cl.[7] .................. A61K 31/216; A61K 31/4402
(52) U.S. Cl. ....................... 514/530; 514/352
(58) Field of Search ................. 514/530, 352

(56) References Cited

U.S. PATENT DOCUMENTS

| | | | |
|---|---|---|---|
| 2,757,124 A | 7/1956 | Wolff | 167/82 |
| 2,798,024 A | 7/1957 | Zappas et al. | 167/82 |
| 3,018,221 A | 1/1962 | Millar et al. | 167/65 |
| 3,061,517 A | 10/1962 | Walter | 167/65 |
| 4,552,899 A | 11/1985 | Sunshine et al. | 514/568 |
| 4,601,714 A | 7/1986 | Burnhill | 604/286 |
| 4,552,899 A | 10/1992 | Sunshine et al. | 514/568 |
| 5,164,398 A | 11/1992 | Sims et al. | 514/282 |
| 5,599,846 A | 2/1997 | Chopdekar et al. | 514/653 |
| 5,663,415 A | 9/1997 | Chopdekar et al. | 560/68 |
| 5,807,579 A | 9/1998 | Vilkov et al. | 424/469 |
| 6,037,358 A | 3/2000 | Gordziel | 514/357 |
| 6,287,597 B1 | 9/2001 | Gordziel | 424/464 |
| 6,306,904 B1 | 10/2001 | Gordziel | 514/530 |
| 6,417,206 B1 | 7/2002 | Leflein et al. | 514/352 |
| 6,462,094 B1 | 10/2002 | Dang et al. | 514/849 |
| 2001/0011104 A1 | 8/2001 | Gordziel | 514/653 |

FOREIGN PATENT DOCUMENTS

| | | |
|---|---|---|
| JP | 39007786 | 5/1964 |
| JP | 64007786 | 8/1993 |
| JP | 06287144 | 1/1995 |

OTHER PUBLICATIONS

Weiler et al., "Randomized, double blind, parallel groups, placebo–controlled study of efficacy and safety of Rynatan in the treatment of allergic rhinits using an acute model," Annals of Allergy, vol. 64(1): 63–67 (1990).
Goldberg et al., "Evaluation of a Prolonged Action Oral Antihistaminic Preparation as Treatment for Allergic Disorders," Clinical Medicine, vol. 72(9): 1475–1479 (1965).
TRIPLE TANNATE, Drug Launches 5/99.
TUSSI–12, Drug Launches 3/99.
TUSSI–12, Drug Launches 12/98.
R–TANNATE, Drug Launches 8/98.
TRIPLE TANNATE, Drug Launches. 1/98.
ATROHIST, Drug Launches. 5/97.
GELHIST, Drug Launches. 5/97.
PHENATAN, Drug Launches 1/97.
TRIOTANN, Drug Launches 12/95.
TRI–TANNATE, Drug Launches 6/95.
RICOBIN–D, Drug Launches 6/95.
RICOBID, Drug Launches 6/95.
QUAD–TUSS TANNATE, Drug Launches 4/95.
TRI–TANNATE, Drug Launches 3/99.
TRITAN, Drug Launches 9/96.
TRI–NATAN, Drug Launches 11/93.
R–TANNATE, Drug Launches 11/93.
TRIN TUSS, Drug Launches 3/93.
TANORAL, Drug Launches 4/92.
HISTATUSS, Drug Launches 7/91.
TRI–TANNATE, Drug Launches 9/87.
TRI–TANNATE, Drug Launches 9/87.
TANORAL, Drug Launches 4/92.
"Robitussin et seq." Physician's Desk Reference, 33rd Ed., 1979, pp. 1424–1425.
Wilson and Grisvold's Textbook of Organic Medicinal and Pharmaceutical Chemistry, Ninth Ed. 1991, pp. 423 & 425.

*Primary Examiner*—Phyllis G. Spivack
(74) *Attorney, Agent, or Firm*—Elliot M. Olstein; Raymond R. Stauffer

(57) ABSTRACT

Tannate compositions consisting of carbetapentane tannate and pyrilamine tannate, which are effective when administered orally for the symptomatic relief of coryza associated with the common cold, sinusitis, allergic rhinitis, unproductive cough and upper respiratory tract conditions, are disclosed.

16 Claims, No Drawings

ANTIHISTAMINIC/ANTITUSSIVE COMPOSITIONS

This application is a continuation of Ser. No. 09/625,422 filed Jul. 25, 2000, now U.S. Pat. No. 6,306,904.

FIELD OF INVENTION

The invention relates to novel antihistaminic and antitussive tannate compositions. The compositions contain as essential ingredients carbetapentane tannate and pyrilamine tannate.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid, the internal ester of gallic acid also frequently referred to as tannin.

Tannic Acid consists of an amorphous powder glistening scales or spongy masses varying in color from yellowish-white to light brown. Tannic acid is very soluble in water, glycerine or alcohol.

Tannic acids are usually obtained from glycosides which consist of several molecules of a tannic acid in combination with glucose.

Commercially available, tannic acid, also known as Tannin, has a complex non-uniform chemistry usually contains from about 5% to about 10% by weight water, has a molecular weight of about 1700 and is typically produced from Turkish or Chinese nutgall.

Carbetapentane, 2-(2-diethylaminoethoxy)ethyl-1 phenylcyclopentane carboxlate is an antitussive compound that is described in U.S. Pat. No. 2,842,585 and is structurally related to caramiphen. Carbetapentane citrate has a melting point of 93° C. and occurs as a white powder freely soluble in water and slightly soluble in alcohol.

Carbetapentane has an atropine-like action that depresses the cough reflex by selective central nervous system depression.

Pyrilamine is one of the oldest and most enduring antihistaminic drugs, known chemically as N-[(4-methoxyphenyl)methyl]-N',N'-dimehthyl-N-2-pyridinyl-1, 2-ethanediamine, its preparation is disclosed in U.S. Pat. No. 2,502,151 and is an oily liquid. Pyrilamines hydrochloride salt is very soluble in water and has a melting point of 143–143.5° C. whereas the maleate salt is slightly soluble in water, benzene and ether and has a melting point of 100–101° C.

Antihistamine compounds in the form of their free bases as well as their salts, e.g. hydrochloride, citrate, maleate, tannate, etc., are well known. Antihistamines in the form of their tannate salts are very desirable because such salts are generally stable and may be combined in such form without any untoward side effects.

Antihistaminics and antitussives in the form of their tannate salts are typically prepared by reacting the free base, e.g. pyrilamine, carbetapentane, etc. with tannic acid in the presence of a volatile solvent, usually isopropanol. Typically, in the conventional isopropanol route, the decongestant or antihistaminic free base and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. Nos. 5,599,846 and 5,663,415.

THE INVENTION

It has now been found that the novel combination of carbetapentane tannate and pyrilamine tannate produces a composition having antitussive and antihistaminic properties superior to the use of either one of the tannate compounds alone.

The compositions of the present invention may be prepared for oral administration in the form of powders, capsules, elixirs, syrups and the preferred forms of tablets formulated so that ideally each tablet contains about 50 mg to about 75 mg, preferably about 60 mg of carbetapentane tannate and about 50 mg to about 75 mg, preferably about 60 mg pyrilamine tannate or suspensions formulated so that ideally each 5 mL (approximately 1 teaspoon) of suspension would contain approximately 20 to 30 mg carbetapentane tannate and an equal amount of pyrilamine tannate.

Tablets containing the unique tannate combination of the present invention are prepared in a conventional manner by the addition of suitable pharmaceutical carriers including fillers, diluents, colorants, lubricants and the like as well as conventional and well known binding and disintegrating agents. A typical tablet composition of the present invention containing starch, dibasic calcium phosphate, coloring, magnesium stearate, methylcellulose, polygalacturoic acid, povidone and talc as described in Example 1 which follows is prepared by well known conventional tabletting techniques such as those disclosed in U.S. Pat. Nos. 3,018,221; 2,798,024 and 2,757,124.

EXAMPLE 1

Carbetapentane Tannate and Pyrilamine Tannate Tablets

| Ingredient | Milligrams per Tablet |
|---|---|
| Carbetapentane Tannate | 60.0 |
| Pyrilamine Tannate | 60.0 |
| Starch, NF | 65.0 |
| Methylcellulose, USP | 150 |
| Polygalactouronic Acid | 32.0 |
| Dibasic Calcium Phosphate, USP, Dihydrate | 65.0 |
| Povidone, USP | 25.0 |
| Talc, USP | 5.4 |
| FD&C Red #40 Aluminum Lake-40% | 3.93 |
| D&C Blue #1 Aluminum Lake-29% | 1.0 |
| Magnesium Stearate, NF | 4.0 |
| Alcohol Specially Denatured 23A 190 Proof | 140[1] |

[1]Not present in the finished tablet product

Suspensions of the compositions of the present invention are prepared in a conventional manner such that each 5 mL (one teaspoon) contains:

| Carbetapentane Tannate | 20–30 mg |
|---|---|
| Pyrilamine Tannate | 20–30 mg |

The suspension formulations additionally contain benzoic acid, coloring, natural and artificial flavors, glycerin, kaolin, magnesium aluminum silicate, methyl paraben, pectin, purified water, saccharin, sodium hydroxide, tannic acid and sucrose or sorbitol.

Example 2, which follows, is illustrative of a typical suspension formulation of the present invention prepared by conventional well known compounding techniques.

EXAMPLE 2

| Ingredient | Milligrams per 5 mL |
| --- | --- |
| Carbetapentane Tannate | 30.0 |
| Pyrilamine Tannate | 30.0[1] |
| Pectin, USP (Medium Viscosity) | 50.0 |
| Kaolin, USP (Colloidal Powder) | 1000 |
| Magnesium Aluminum Silicate, NF | 35.0 |
| Benzoic Acid, USP | 10.0 |
| Methylparaben, NF | 5.0 |
| Sucrose, NF | 1000 |
| Saccharin Sodium, USP | 0.75 |
| Glycerin, USP | 225 |
| Flavor Black Currant Imitation | 0.91 |
| Flavor Strawberry with Other Natural Flavors | 2.28 |
| Purple Shade "R" Dye | 0.45 |
| FD&C Red #3 Dye | 0.8 |
| FD&C Yellow #5 | 0.3 |
| Sodium Hydroxide Solution-50% | 3.17[2] |
| Purified Water, USP (Deionized) adjust to | 5 ml |

[1] 5% excess added during manufacturing
[2] The quantity of Sodium Hydroxide Solution may be varied depending on the pH of the Kaolin used in the batch. Tannic acid may also be used in lieu of sodium hydroxide solution for pH adjustment.
[3] Sodium Citrate. USP, Dihydrate and Citric Acid, USP, Anhydrous may also be included in the formula for pH adjustment.

For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A therapeutic composition in the form of a tablet for the symptomatic treatment of coryza associated with the common cold, sinusitis, allergic rhinitis, unproductive cough, and upper respiratory tract conditions in warm-blooded animals in need of such treatment, said composition including active ingredients consisting of from about 50 mg to about 75 mg of carbetapentane tannate and from about 50 mg to about 75 mg of pyrilamine tannate.

2. The composition of claim 1 wherein said carbetapentane tannate is present in said tablet in an amount of about 60 mg.

3. The composition of claim 1, wherein said pyrilamine tannate is present in said tablet in an amount of about 60 mg.

4. The composition of claim 3, wherein said carbetapentane tannate is present in said tablet in an amount of about 60 mg.

5. A therapeutic composition in the form of a suspension for the symptomatic treatment of coryza associated with the common cold, sinusitis, allergic rhinitis, unproductive cough, and upper respiratory tract conditions in warm-blooded animals in need of such treatment, said composition including active ingredients consisting of from about 20 mg to about 30 mg of carbetapentane tannate and of from about 20 mg to about 30 mg of pyrilamine tannate in each 5 ml of said suspension.

6. The composition of claim 5 wherein said carbetapentane tannate is present in said suspension in an amount of 30 mg in each 5 ml of said suspension.

7. A The composition of claim 5 wherein said pyrilamine tannate is present in said suspension in an amount of 30 mg in each 5 ml of said suspension.

8. The composition of claim 7 wherein said carbetapentane tannate is present in an amount of 30 mg in each 5 ml of said suspension.

9. A method for symptomatically treating and relieving the distress of coryza associated with the common cold, sinusitis, allergic rhinitis, unproductive cough, and upper respiratory tract conditions in warm-blooded animals, which comprises orally administering to warm-blooded animals in need of such treatment a therapeutic amount of a composition in tablet form that includes active ingredients consisting of about 50 mg to about 75 mg of carbetapentane tannate and from about 50 mg to about 75 mg of pyrilamine tannate.

10. The method of claim 9 wherein said carbetapentane tannate is present in said tablet in an amount of about 60 mg.

11. The method of claim 9 wherein said pyrilamine tannate is present in said tablet in an amount of about 60 mg.

12. The method of claim 11 wherein said carbetapentane tannate is present in said tablet in an amount of about 60 mg.

13. A method for symptomatically treating and relieving the distress of coryza associated with the common cold, sinusitis, allergic rhinitis, unproductive cough, and upper respiratory tract conditions in warm-blooded animals, which comprises orally administering to warm-blooded animals in need of such treatment a therapeutic amount of a composition in suspension form that includes active ingredients consisting of from about 20 mg to about 30 mg of carbetapentane tannate and of from about 20 mg to about 30 mg of pyrilamine tannate in each 5 ml of said suspension.

14. The method of claim 13 wherein said carbetapentane tannate is present in said suspension in an amount of 30 mg in each 5 ml of said suspension.

15. The method of claim 13, wherein said pyrilamine tannate is present in said suspension in an amount of 30 mg in each 5 ml of said suspension.

16. The method of claim 15 wherein said carbetapentane tannate is present in an amount of 30 mg in each 5 ml of said suspension.

* * * * *

UNITED STATES PATENT AND TRADEMARK OFFICE
CERTIFICATE OF CORRECTION

PATENT NO. : 6,586,469 B2
DATED : July 1, 2003
INVENTOR(S) : Gordziel

It is certified that error appears in the above-identified patent and that said Letters Patent is hereby corrected as shown below:

<u>Title page,</u>
Item [57], ABSTRACT,
Line 1, after "consisting" and before "of" insert -- essentially --

Signed and Sealed this

Eleventh Day of May, 2004

JON W. DUDAS
*Acting Director of the United States Patent and Trademark Office*